US012447100B2

(12) United States Patent
Hanson

(10) Patent No.: US 12,447,100 B2
(45) Date of Patent: Oct. 21, 2025

(54) COLD TUB WITH WARMING POCKETS

(71) Applicant: Adam Hanson, Big Lake, MN (US)

(72) Inventor: Adam Hanson, Big Lake, MN (US)

( * ) Notice: Subject to any disclaimer, the term of this patent is extended or adjusted under 35 U.S.C. 154(b) by 349 days.

(21) Appl. No.: 18/316,054

(22) Filed: May 11, 2023

(65) Prior Publication Data

US 2024/0374416 A1 Nov. 14, 2024

(51) Int. Cl.
*A61H 33/00* (2006.01)
*A61F 7/00* (2006.01)

(52) U.S. Cl.
CPC ....... *A61H 33/6005* (2013.01); *A61F 7/0053* (2013.01); *A61H 33/0095* (2013.01); *A61F 2007/0036* (2013.01); *A61F 2007/0045* (2013.01); *A61F 2007/0054* (2013.01); *A61H 2201/0214* (2013.01); *A61H 2201/0242* (2013.01)

(58) Field of Classification Search
CPC ............ A61H 33/6005; A61H 33/0095; A61F 2007/0036; A61F 2007/0045; A61F 7/0053
See application file for complete search history.

(56) References Cited

U.S. PATENT DOCUMENTS

| | | | | |
|---|---|---|---|---|
| 4,376,437 | A * | 3/1983 | Sundheim | A61M 35/30 607/104 |
| 4,761,838 | A * | 8/1988 | Hargrove | A61H 33/0095 4/514 |
| 8,393,019 | B1 * | 3/2013 | Cavuoti | A61H 33/0095 4/546 |
| 2022/0218519 | A1 * | 7/2022 | Karika | A61F 7/086 |
| 2023/0008389 | A1 * | 1/2023 | Kwacz | A47K 3/022 |

* cited by examiner

*Primary Examiner* — James M Kish
(74) *Attorney, Agent, or Firm* — Robert T. Vorhoff

(57) ABSTRACT

The present invention provides a cold tub with warming pockets which provides a cold-therapy tub with the benefit of warming pockets for the hands and feet to prevent pain and numbness of the hands and feet during use.

20 Claims, 9 Drawing Sheets

SECTION A-A

COLD TUB WITH WARMING POCKETS

FIELD OF THE INVENTION

The present invention relates to tubs or spas, specifically tubs or spas that are used to provide cold-water immersion therapy. More particularly, the present invention provides a cold-water therapy tub or spa with warming pockets for hands and feet.

BACKGROUND OF THE INVENTION

It is widely accepted that cold-water therapy can be used to relieve muscle soreness, swelling, and joint pain brought about by prolonged physical exertion. Athletes, trainers, and physical therapists commonly use cold-water baths or ice baths to alleviate inflammation of muscles and other bodily tissues following an intense workout or therapy session.

Cold-water therapy tubs are known in the art. In their most basic form, these tubs consist of an uninsulated metal, plastic, or molded tub that is filled with ice or an ice water slurry. Some prior art tubs are insulated and use a chiller for circulating cold water throughout the tub, similar to the manner in which a hot tub circulates heated water. Still others employ provisions for circulating either hot or cold water, or a combination of both. For example:

U.S. Pat. No. 3,366,110, by Gaylord, Jr., discloses a method and apparatus for providing a continuous flow of a physiological solution as irrigation treatment for burn patients;

U.S. Pat. No. 4,761,838, by Hargrove, discloses a spa system having separate chambers, with one chamber providing hot aerated water and the other providing cold quiet water;

U.S. Pat. No. 5,241,958, by Noeldner, discloses a therapeutic whirlpool unit that sequentially introduces and removes water having contrasting temperature levels;

U.S. Pat. No. 8,393,019, by Cavuoti, discloses a spa system featuring an immersion tank with a hot reservoir, a cold reservoir, and a mixer reservoir to change the temperature of the liquid in the immersion tank;

U.S. patent application Ser. No. 11/379,859, by Na, et al., discloses a spa with a heat pump for both heating and cooling the water within the spa tub;

U.S. patent application Ser. No. 11/401,752, by Reynolds, II, discloses a spa system with water heating and cooling devices coupled in series;

U.S. patent application Ser. No. 15/806,211, by Howell, discloses an insulated therapy tub; and, U.S. patent application Ser. No. 17/319,275, by Foy, et al., discloses a spa with a rotational molded shell having a cavity between the spa basin and the peripheral wall, with at least one opening leading to the cavity;

Likewise, devices used for cooling and heating appendages are known in the art. For example:

U.S. Pat. No. 3,565,065, by Biggs, Jr., discloses a hydrotherapy tank for treating the forearm and hand;

U.S. Pat. No. 4,217,892, by Brill, discloses a hydrotherapy tank for massaging parts of the body using pulsating streams of water;

U.S. patent application Ser. No. 13/208,324, by Kingsley, discloses a housing with a cavity configured to accept at least a portion of a user's body part and a quantity of liquid for surrounding the body part;

U.S. patent application Ser. No. 14/821,709, by Ruetenik, discloses an ice boot spa system to allow leg and ankle cooling; and, U.S. patent application Ser. No. 17/610,560, by Karika, et al., discloses an appendage cooling and heating system.

One drawback of existing cold-water therapy tubs and other devices is that the hands and feet cool more rapidly than the rest of the body, which can result in numbness and pain. Therefore, a need exists in the field for a cold-water therapy tub or spa that allows the benefit of cold-water immersion therapy without the drawback of pain and numbness in the hands and feet.

BRIEF SUMMARY OF THE INVENTION

The preferred embodiment of the present invention solves the aforementioned problem in a straightforward and simple manner by providing a novel cold-water therapy tub or spa that incorporates warming chambers or pockets for the hands and feet. The cold-water therapy tub of the present invention incorporates a chiller unit and system to cool the water for circulation throughout the tub, with a separate heating unit and system to distribute warm water to pockets for the hands and feet.

BRIEF DESCRIPTION OF THE DRAWING

For a further understanding of the nature and objects of the present invention, reference should be had to the following description taken in conjunction with the accompanying drawing in which like parts are given like reference numerals, and wherein.

DETAILED DESCRIPTION OF THE INVENTION

Figure 1:
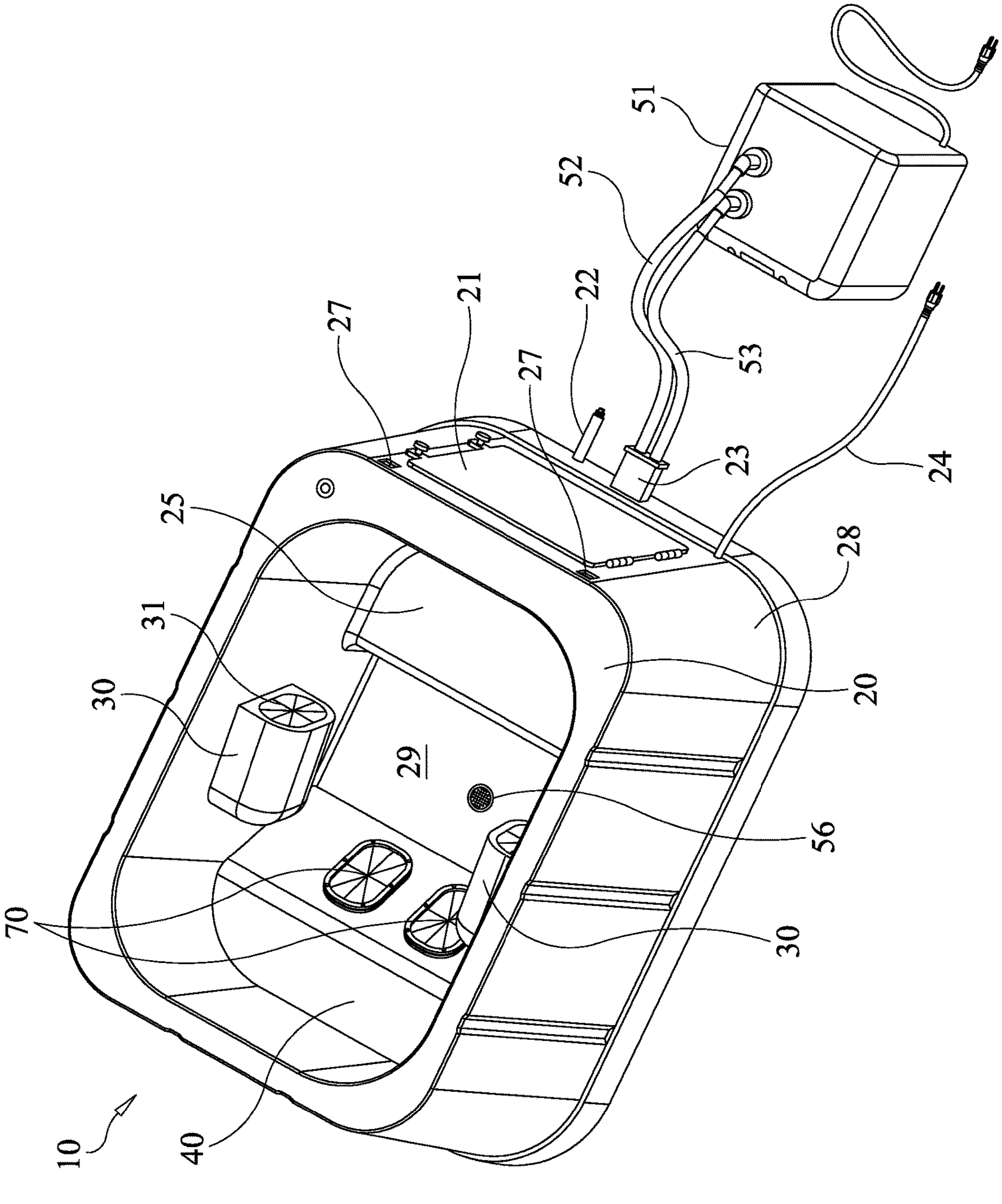
FIG. 1 depicts an oblique perspective view of the cold therapy tub of the present invention.
Figure 2:
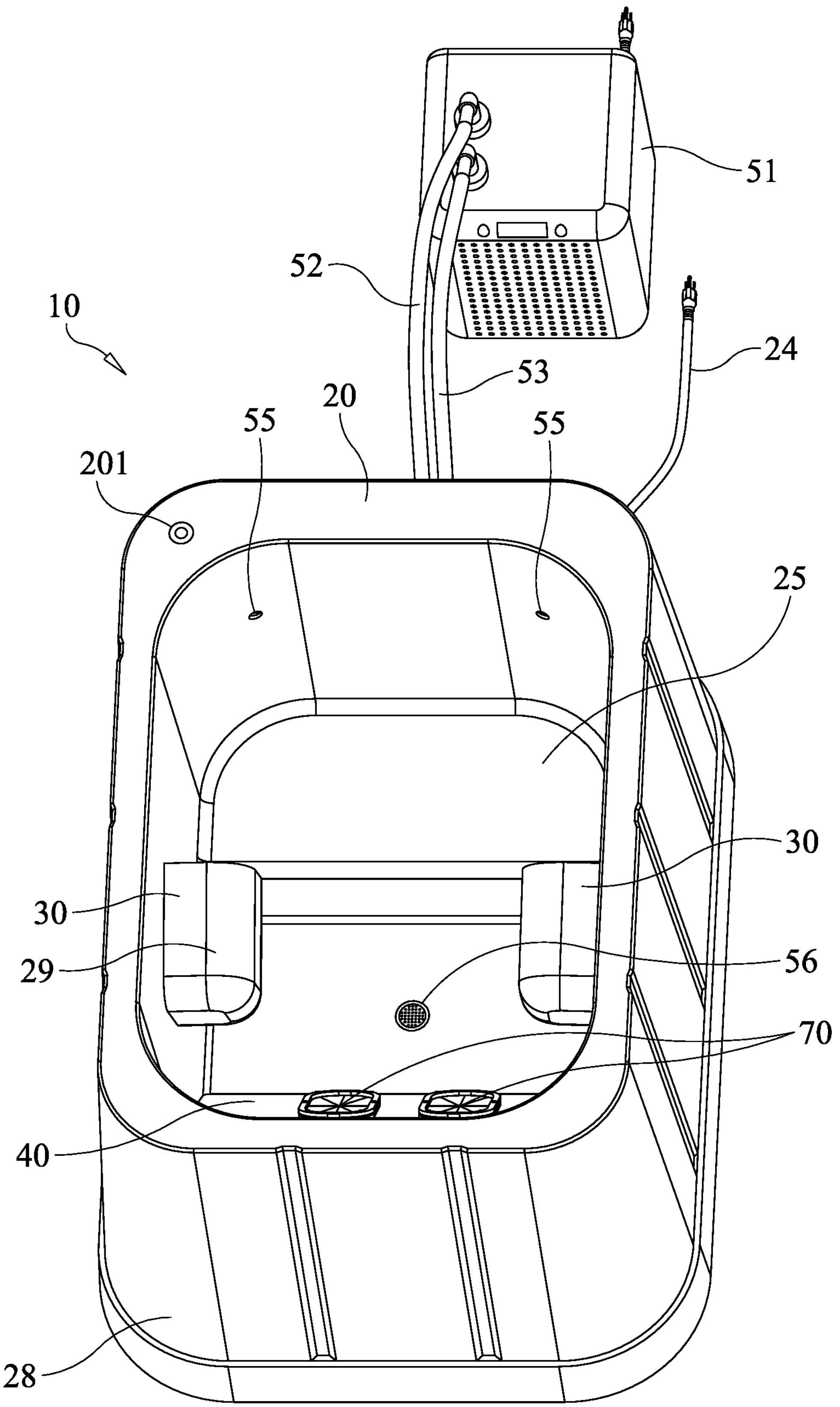
FIG. 2 depicts an overhead perspective view of the cold therapy tub of the present invention.
Figure 3:
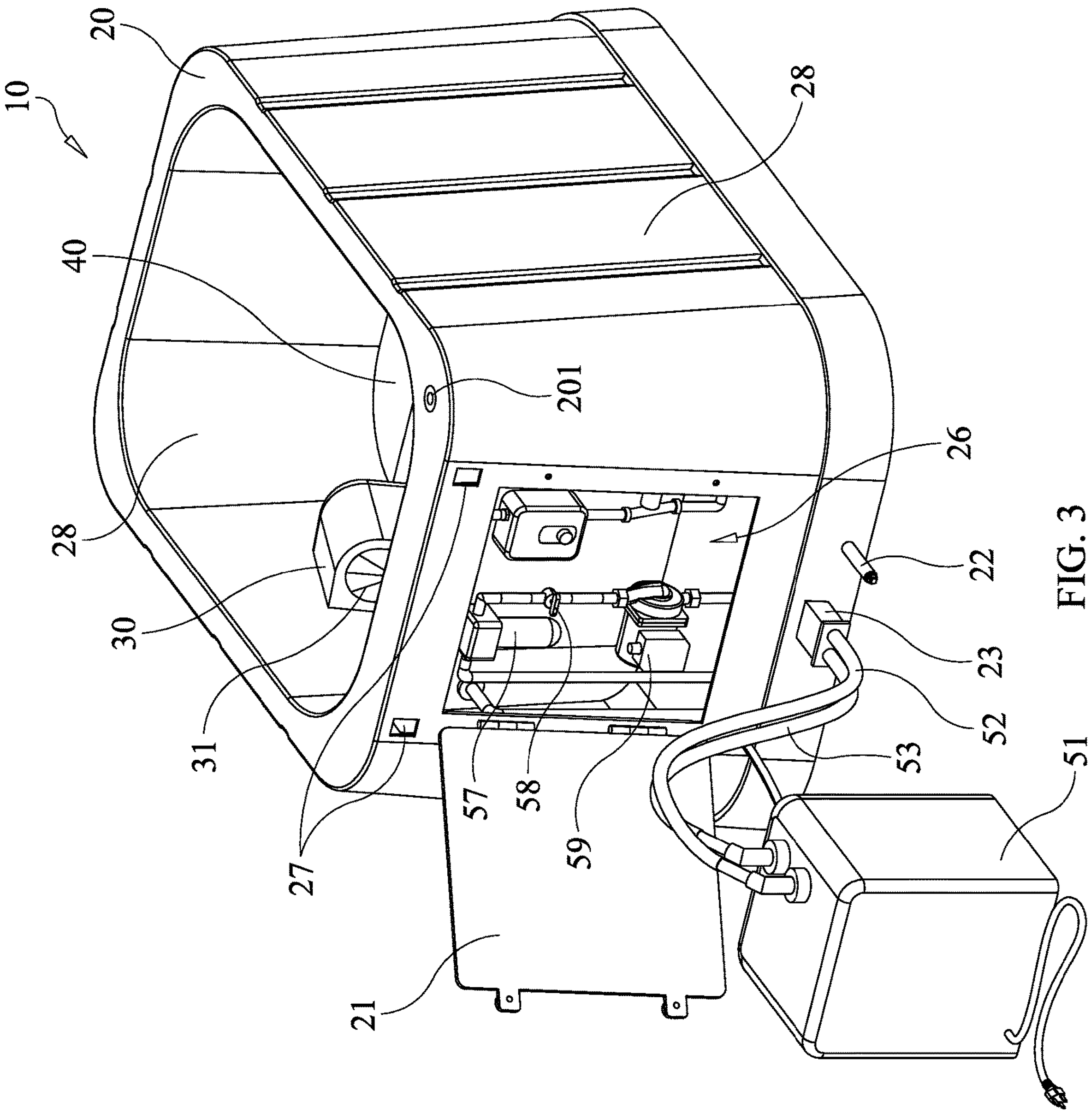
FIG. 3 depicts a rear perspective view of the cold therapy tub of the present invention showing the mechanical service compartment.

Referring now to FIGS. 1, 2, and 3 of the drawing, the cold tub with warming pockets of the present invention is designated generally by the numeral 10. Cold tub 10 comprises tub enclosure 20, hand warming pockets 30, and foot warming pocket 40. Tub enclosure 20 is generally rectangular in shape in the preferred embodiment, but it may be of any desired configuration that allows for suitable placement of hand warming pockets 30 and foot warming pocket 40 to accommodate a person's hands and feet. Tub enclosure 20 further comprises service compartment door 21, drain fitting 22, cold-water connector 23, electrical cord 24, integral seat 25, service compartment 26, ladder mounts 27, walls 28, and floor 29.

Tub enclosure 20 may be constructed by using a rotational molding process, vacuum or thermo-formed acrylic, or fiberglass and gelcoat. Walls 28 are essentially hollow to accommodate cold-water system 50 and hot-water system 60, and are insulated with closed cell polyurethane foam, or other suitable insulating material as is known in the art. Tub enclosure 20 may also incorporate LED lighting or other spa accessories known in the art.

In the preferred embodiment, integral seat 25 is located at one end of the interior of tub enclosure 20 with service compartment door 21 attached to the corresponding exterior of wall 28 through means of hinges and screw knobs to provide access to service compartment 26. Drain fitting 22, cold-water connector 23, and electrical cord 24 pass through wall 28 below service compartment door 21. Ladder mounts 27 are integrally molded into the exterior of wall 28 proximate to integral seat 25, providing means for attachment of optional steps or a ladder if desired to facilitate entry and exit for tub enclosure 20.

Hand warming pockets 30 are located on the interior of walls 28 adjacent to integral seat 25, and foot warming pocket 40 is located on floor 29 at the end of tub enclosure 20 opposite to integral seat 25. Hand warming pockets 30 and foot warming pocket 40 are affixed to tub enclosure 20 through means of screws or other suitable fasteners. Hand warming pockets 30 further comprise hand opening 31, which is adapted to accommodate insertion of a person's hand, and pocket seal 70. Foot warming pocket 40 further comprises foot openings 41, which are adapted to accommodate insertion of a person's feet, and pocket seals 70.

Figure 4:
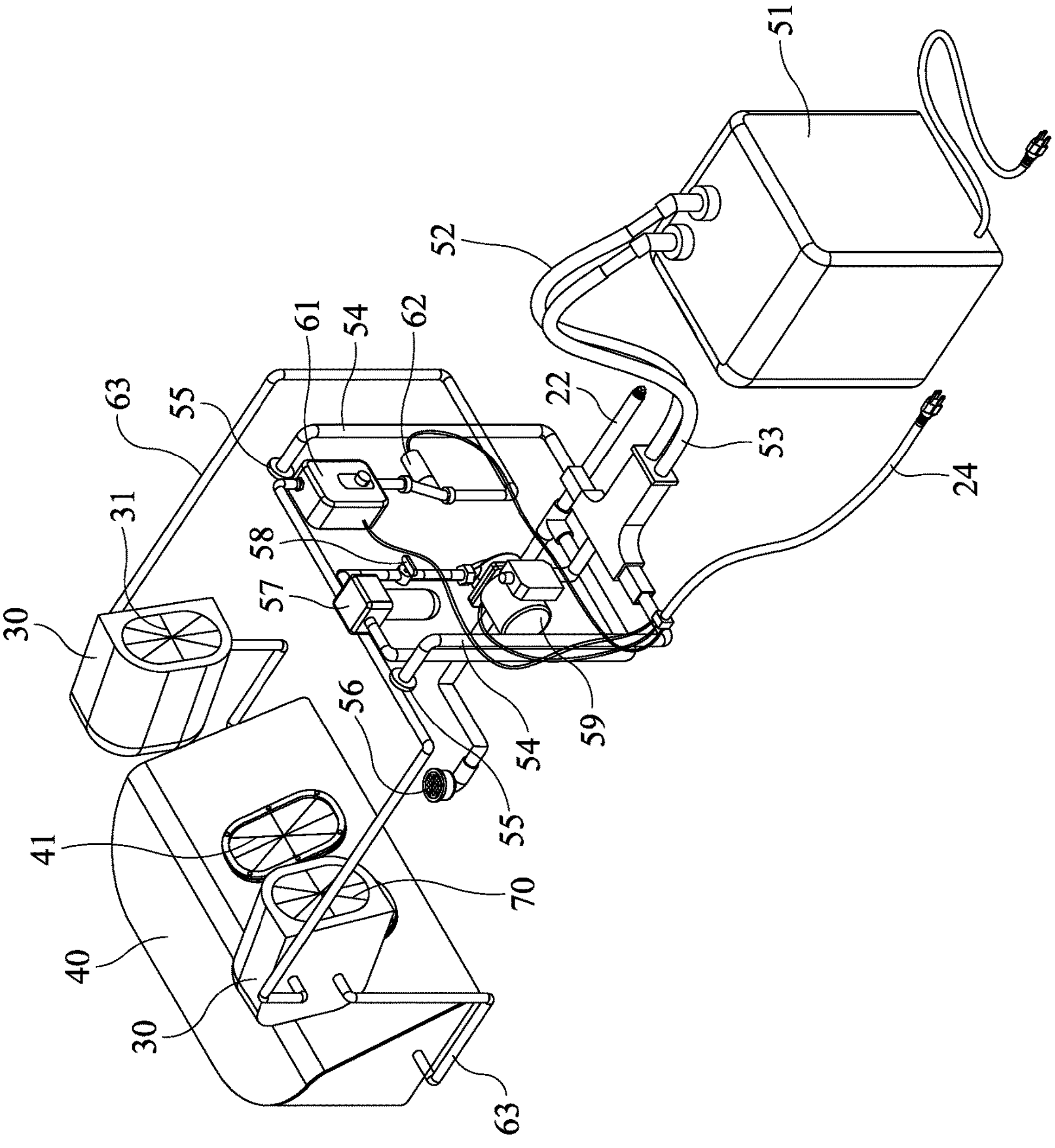
FIG. 4 depicts a component view of the cold and hot-water systems of the present invention.
Figure 5:
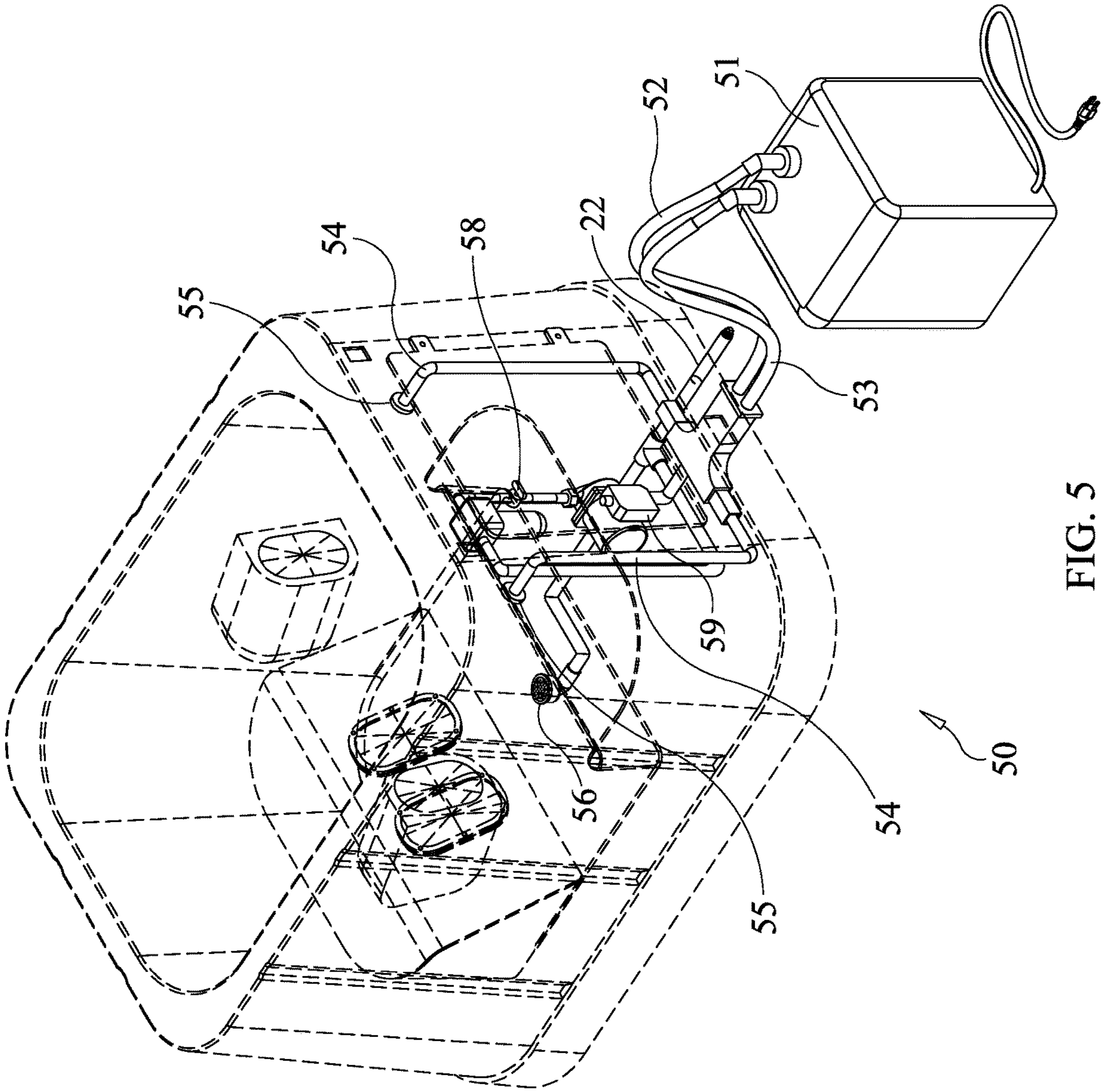
FIG. 5 depicts a component view of the cold-water system of the present invention.
Figure 6:
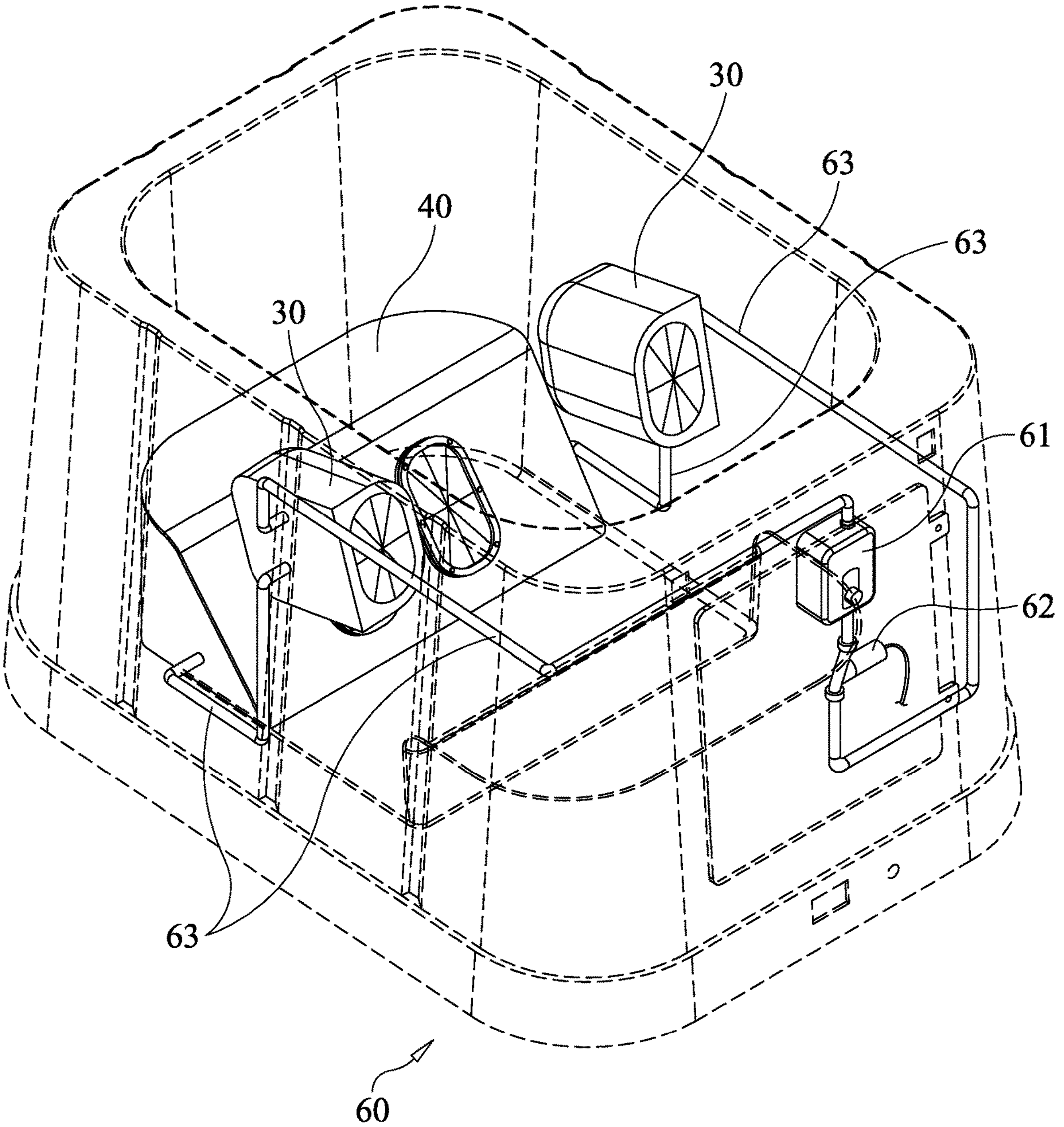
FIG. 6 depicts a component view of the hot-water system of the present invention.

Referring now to FIGS. 4, 5, and 6, cold therapy tub 10 further comprises cold-water system 50 and hot-water system 60. Cold-water system 50 comprises chiller unit 51, chiller feed line 52, chiller return line 53, cold-water lines 54, fittings 55, drain 56, filter 57, ball valve 58, and cold-water pump 59. Cold water is circulated throughout tub enclosure 20 by cold-water system 50. In the preferred embodiment, chiller 51 is a self-contained unit that is externally connected to cold-water connecter 23. Chiller 51 cools water to a desired temperature in the range of 39 degrees to 65 degrees Fahrenheit. Cold water is then supplied to tub enclosure 20 though chiller feed line 52, which is attached to cold-water connector 23 by means of quick-release connectors, and routed through cold-water lines 54 to fittings 55. Cold-water lines 54 may be rigid polyvinyl chloride (PVC) pipe, cross-linked polyethylene (PEX) tubing, flexible PVC hose, or other suitable liquid conduit as is known in the art. Fittings 55 are typical spa jets or tub fittings as are known in the art. In the preferred embodiment, cold-water pump 59 is a high-efficiency circulation pump. Cold-water pump 59 draws water from drain 56, through filter 57 and ball valve 58, and discharges filtered water to chiller 51 through cold-water connector 23 and chiller return line 53.

Hot-water system 60 comprises water heater 61, hot-water pump 62, hot-water lines 63, hand warming pockets 30, and foot warming pocket 40. Warm water is circulated through hand warming pockets 30 and foot warming pocket 40 by hot-water system 60. Hot-water system 60 is a closed system, with hand warming pockets 30 connected to foot warming pocket 40, water heater 61, and hot-water pump 62 by hot-water lines 63. Hot-water lines 63 may be rigid PVC pipe, PEX tubing, flexible PVC hose, or other suitable liquid conduit as is known in the art. Hot water lines 63 are routed through walls 28 of tub enclosure 20 and are encased in the insulating material of walls 28. Hot water lines 63 are connected to hand warming pockets 30 and foot warming pocket 40 through walls 28 of tub enclosure 20 by bulkhead fittings or other suitable means as are known in the art. In the preferred embodiment, water heater 61 is a flow-activated tankless water heater, which heats water to a desired temperature in the range of 65 degrees to 85 degrees Fahrenheit, and hot-water pump 62 is a high-efficiency circulation pump. Hot-water pump 62 circulates heated water from water heater 61 through hot-water lines 63 to right hand warming pocket 30, foot warming pocket 40, left hand warming pocket 30, and back to water heater 61.

Filter 57, ball valve 58, cold-water pump 59, water heater 61, and hot-water pump 62 are housed in service compartment 26. Switch 201 is electrically connected to cold-water pump 59, hot water-pump 62, and electrical cord 24, such that activation of switch 201 provides electrical power to cold-water pump 59 and hot-water pump 62. In the preferred embodiment, switch 201 is a waterproof switch mounted to wall 28 proximate to integral seat 25.

Figure 7A:
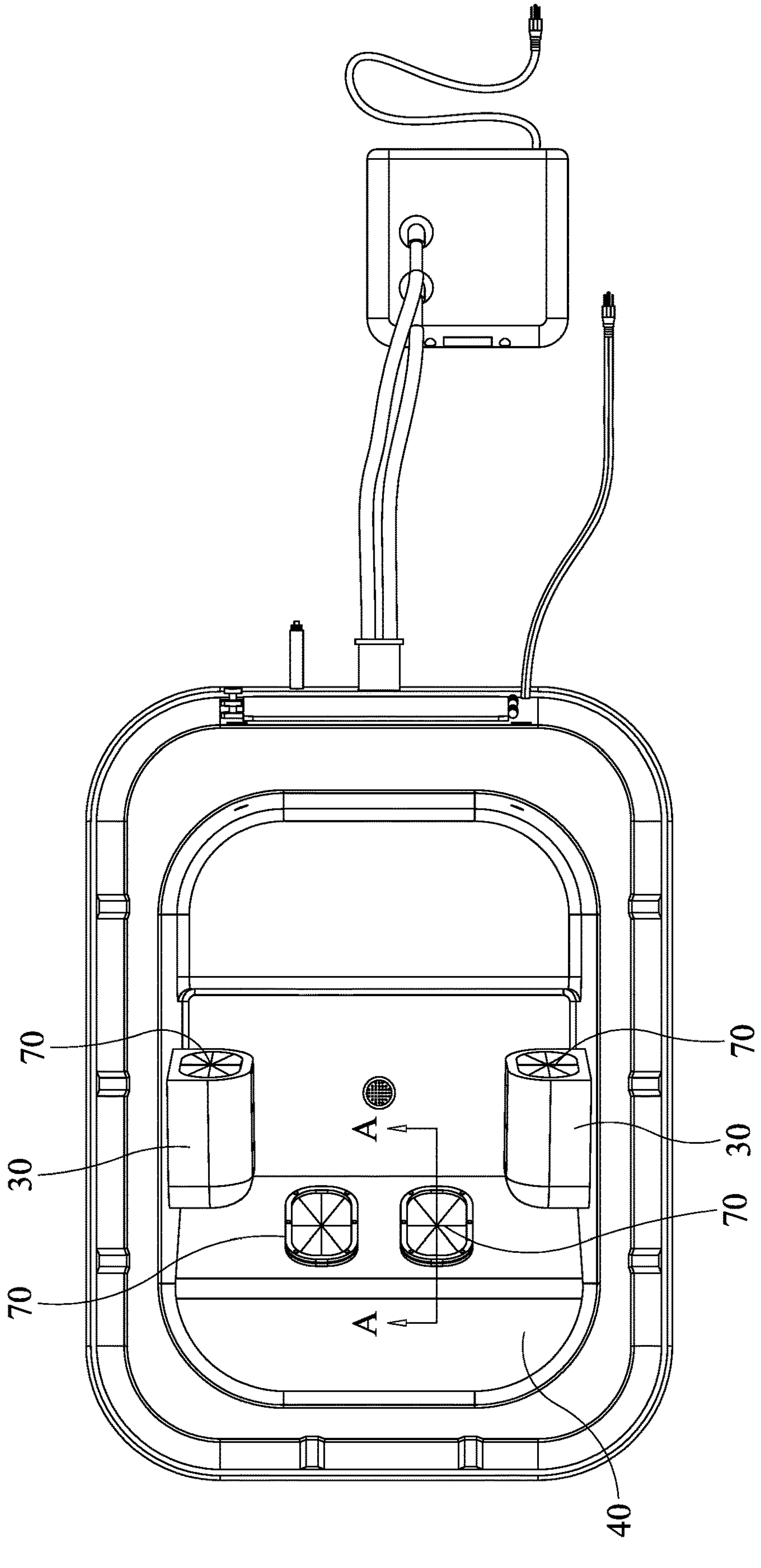
FIG. 7A depicts a top view of the present invention showing the warming pockets.
Figure 7B:
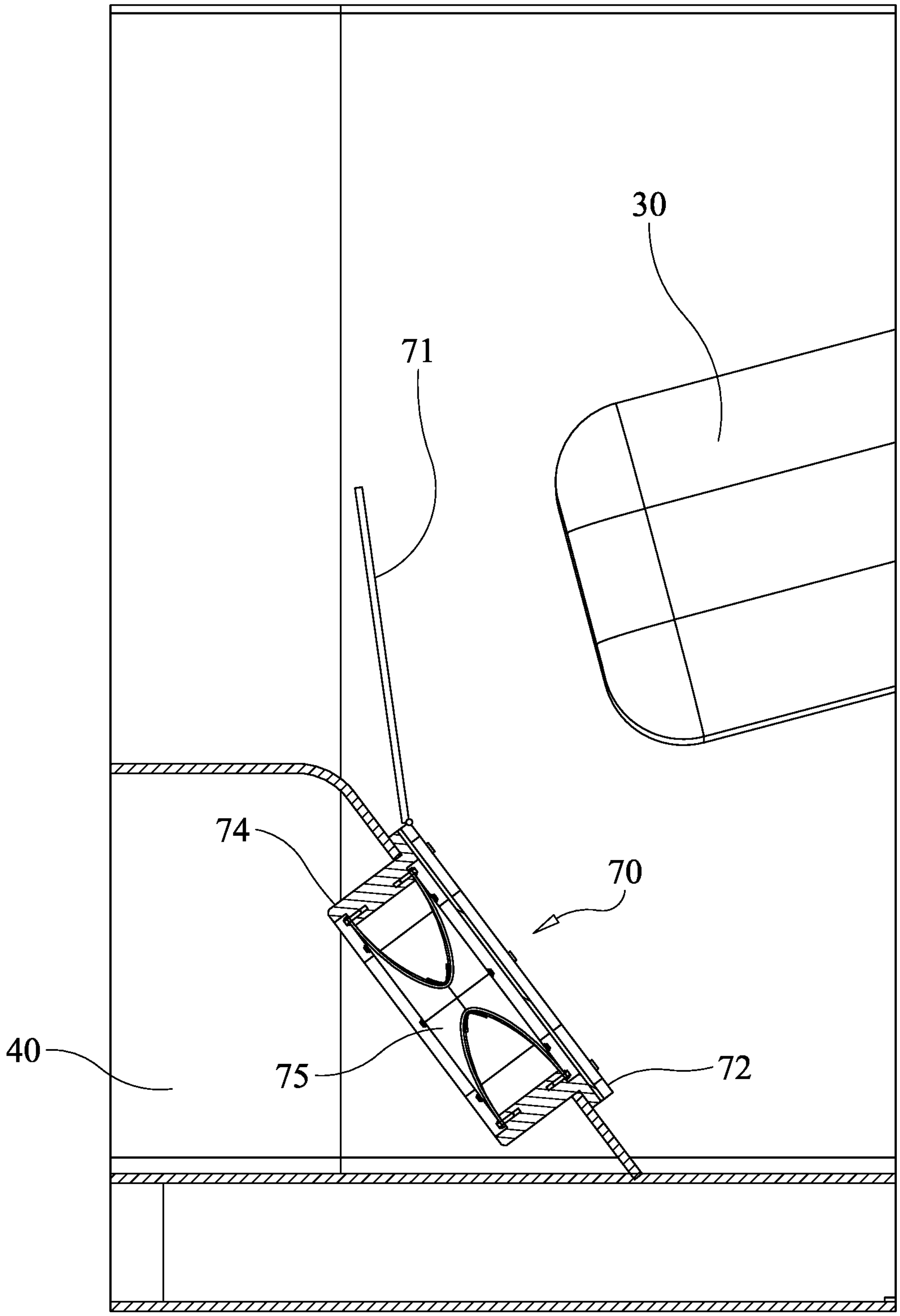
FIG. 7B depicts a cutaway view of the foot pocket of the present invention; and, FIG. 7C depicts an exploded view of the seals for the warming pockets of the preferred embodiment of the present invention.
Figure 7C:
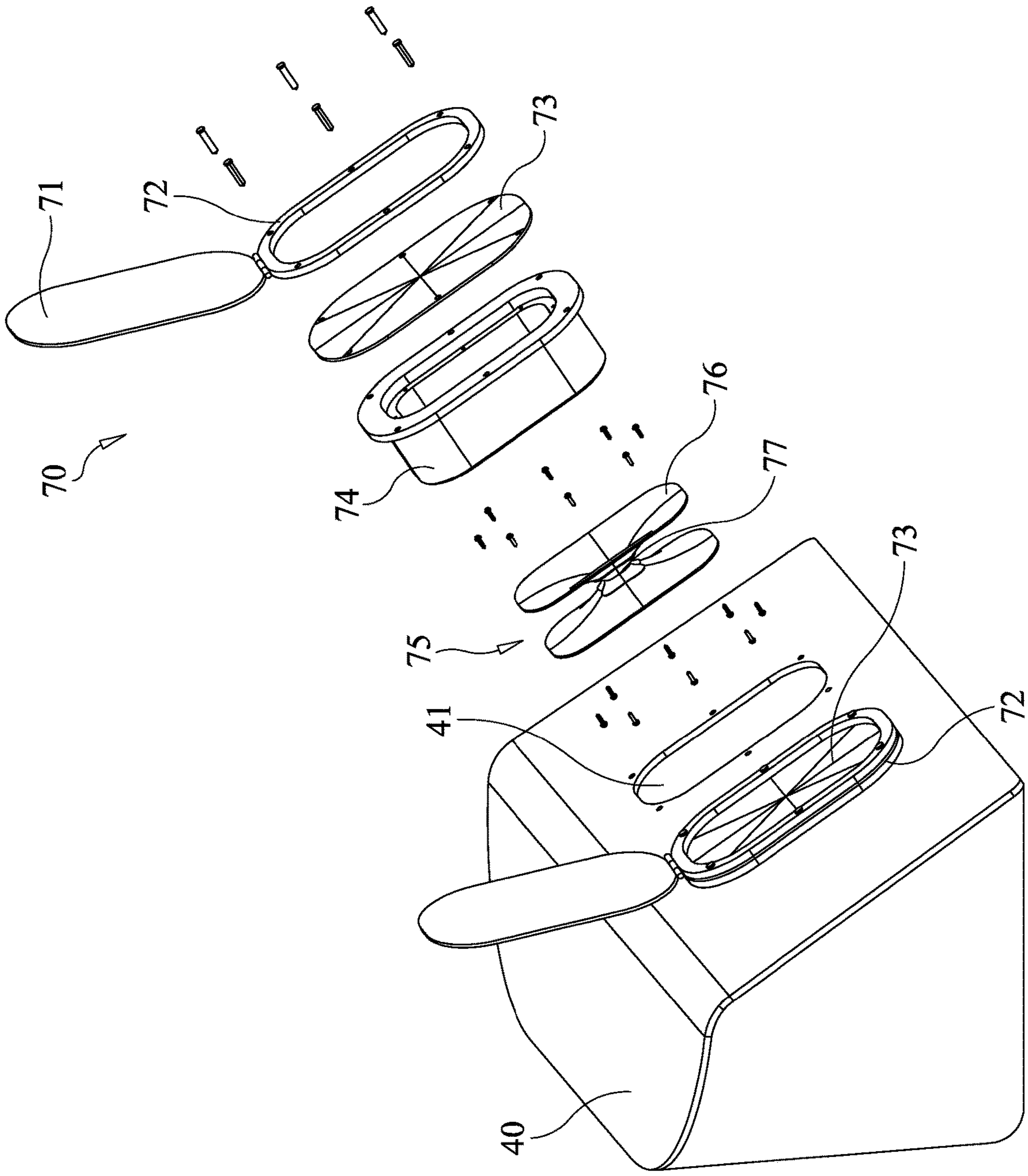

Referring now to FIGS. 7A, 7B, and 7C, hand warming pockets 30 and foot warming pocket 40 further comprise pocket seals 70. Pocket seals 70 comprise cover 71, bezel 72, baffle 73, housing 74, and elastic seal 75.

In the preferred embodiment, pocket seals 70 are essentially oval in shape and are installed in hand openings 31 and foot openings 41 using screws or other suitable fasteners. Pocket seals 70 prevent mixing of cold water in tub enclosure 20 with warm water from hot-water system 60 by means of elastic seal 75, which comprises waterproof membrane 76 and elastic band 77. Waterproof membrane 76 is essentially a hollow sleeve, which is gathered in the center by elastic band 77 and affixed at the ends to the inside of housing 74 by adhesive or other water tight means, such that elastic band 77 fits snugly around a person's wrist or ankle and waterproof membrane 76 inhibits the passage of water through housing 74. Housing 74 and elastic seal 75 are inserted into and attached to cutouts in hand warming pockets 30 and foot pocket 40 through screws or other suitable fastening means. Pocket seals 70 further prevent mixing of cold water in tub enclosure 20 with warm water from hot-water system 60 by means of baffle 73, which is made of rubber, neoprene, or other suitable material as is known in the art to minimize the flow of water into and out of hand warming pockets 30 and foot warming pocket 40. Baffle 73 is provided with radial slits or flaps to accommodate insertion of a hand or foot. Baffle 73 is held in place by bezel 72, which is secured to housing 74 by screws or other suitable fastening means. Pocket seals 70 further comprise cover 71, which is hingedly attached to bezel 72, enabling cover 71 to be closed over bezel 72 when hand warming pockets 30 and foot warming pocket 40 are not in use, further preventing mixing of cold water in tub enclosure 20 with warm water from hot-water system 60.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

The invention claimed is:

1. A cold tub with warming pockets, comprising:

a tub enclosure;

hand warming pockets;

a foot warming pocket;

a cold-water system for circulating cold water throughout the tub enclosure; and a hot-water system for circulating warm water to the hand warming pockets and foot warming pocket.

2. The cold tub with warming pockets of claim 1, wherein said hot-water system further comprises a heater, a hot-water pump, and hot water lines.

3. The cold tub with warming pockets of claim 2, wherein said hand warming pockets are attached to the sides of the tub enclosure, said foot warming pocket is attached to the floor of the tub enclosure, and said hand warming pockets and foot warming pocket are connected to hot water lines to facilitate the circulation of warm water through said hand warming pockets and foot warming pocket.

4. The cold tub with warming pockets of claim 1, wherein said cold-water system comprises a chiller, a filter, a cold-water pump, and cold-water lines.

5. The cold tub with warming pockets of claim 4, wherein said cold-water system further comprises jets connected to said cold-water lines to facilitate circulation of cold water throughout the tub enclosure.

6. The cold tub with warming pockets of claim 1, wherein said hand warming pockets and foot warming pocket comprise seals to prevent mixing of cold water from the tub enclosure with warm water in the hand warming pockets and foot warming pocket.

7. The cold tub with warming pockets of claim 6, wherein said seals each comprise an elastic seal, a baffle, and a cover.

8. The cold tub with warming pockets of claim 1, wherein the temperature of said cold-water system is adjustable from 39 degrees Fahrenheit to 65 degrees Fahrenheit and the temperature of said hot-water system is adjustable from 65 degrees Fahrenheit to 85 degrees Fahrenheit.

9. A cold tub with warming pockets, comprising:
- a tub enclosure;
- hand warming pockets;
- a foot warming pocket;
- a cold-water system for circulating cold water throughout the tub enclosure;
- a hot-water system for circulating warm water to the hand warming pockets and foot warming pocket;
- wherein said cold-water system further comprises a chiller, a filter, a cold-water pump, and cold-water lines; and
- wherein said hot-water system further comprises a heart, a hot-water pump and hot water lines.

10. The cold tub with warming pockets of claim 9, wherein said hand warming pockets and foot warming pocket comprise seals to prevent mixing of cold water from the tub enclosure with warm water in the hand warming pockets and foot warming pocket.

11. The cold tub with warming pockets of claim 10, wherein said seals each comprise an elastic seal, a baffle, and a cover.

12. The cold tub with warming pockets of claim 9, wherein said hand warming pockets are attached to the sides of the tub enclosure, said foot warming pocket is attached to the floor of the tub enclosure, and said hand warming pockets and foot warming pocket are connected to hot water lines to facilitate the circulation of warm water through the hot-water system.

13. The cold tub with warming pockets of claim 9, wherein said cold-water system further comprises jets connected to said cold-water lines to facilitate circulation of cold water throughout the tub enclosure.

14. The cold tub with warming pockets of claim 9, wherein the temperature of said cold-water system is adjustable from 39 degrees Fahrenheit to 65 degrees Fahrenheit and the temperature of said hot-water system is adjustable from 65 degrees Fahrenheit to 85 degrees Fahrenheit.

15. A cold tub with warming pockets, comprising:
- a tub enclosure;
- hand warming pockets;
- a foot warming pocket;
- a cold-water system for circulating cold water throughout the tub enclosure; and
- a hot-water system for circulating warm water to the hand warming pockets and foot warming pocket;
- wherein said cold-water system further comprises a chiller, a filter, a cold-water pump, and cold-water lines;
- wherein said hot-water system further comprises a heart, a hot-water pump and hot water lines; and
- wherein said hand warming pockets and foot warming pocket comprise seals to prevent mixing of cold water from the tub enclosure with warm water in the hand warming pockets and foot warming pocket.

16. The cold tub with warming pockets of claim 15, wherein said seals each comprise an elastic seal, a baffle, and a cover.

17. The cold tub with warming pockets of claim 16, wherein said hand warming pockets are attached to the sides of the tub enclosure, said foot warming pocket is attached to the floor of the tub enclosure, and said hand warming pockets and foot warming pocket are connected to hot water lines to facilitate the circulation of warm water through the hot-water system.

18. The cold tub with warming pockets of claim 17, wherein said cold-water system further comprises jets connected to said cold-water lines to facilitate circulation of cold water throughout the tub enclosure.

19. The cold tub with warming pockets of claim 18, wherein the temperature of said cold-water system is adjustable from 39 degrees Fahrenheit to 65 degrees Fahrenheit and the temperature of said hot-water system is adjustable from 65 degrees Fahrenheit to 85 degrees Fahrenheit.

20. The cold tub with warming pockets of claim 15, wherein the temperature of said cold-water system is adjustable from 39 degrees Fahrenheit to 65 degrees Fahrenheit and the temperature of said hot-water system is adjustable from 65 degrees Fahrenheit to 85 degrees Fahrenheit.

* * * * *